United States Patent [19]
Menard

[11] Patent Number: 5,562,793
[45] Date of Patent: Oct. 8, 1996

[54] METHODS AND APPARATUS FOR MAKING MULTI-LAYER ABSORBENT PRODUCTS

[75] Inventor: Michael J. Menard, Holicong, Pa.

[73] Assignee: McNeil-PPC, Skillman, N.J.

[21] Appl. No.: 452,449

[22] Filed: May 26, 1995

Related U.S. Application Data

[62] Division of Ser. No. 204,127, Mar. 2, 1994.

[51] Int. Cl.⁶ ........................................... B32B 31/04
[52] U.S. Cl. .................... 156/263; 156/264; 156/227; 604/385.1
[58] Field of Search ................................ 156/269, 270, 156/227, 263, 276, 324, 264, 259, 260, 204; 604/385.1, 359, 374, 378, 379

[56] References Cited

U.S. PATENT DOCUMENTS

| | | | |
|---|---|---|---|
| 4,670,011 | 6/1987 | Mesek | 604/378 |
| 4,690,719 | 9/1987 | Lucas et al. | 156/201 |
| 4,760,764 | 8/1988 | De Jonckheere et al. | 83/23 |
| 4,960,477 | 10/1990 | Mesek | 156/209 |
| 5,110,386 | 5/1992 | Ochi et al. | 156/204 |

*Primary Examiner*—David A. Simmons
*Assistant Examiner*—Linda L. Gray
*Attorney, Agent, or Firm*—James P. Barr

[57] ABSTRACT

Improved methods and apparatus for forming absorbent products and the improved absorbent products formed thereby are disclosed. In a first embodiment of the present invention, a rotary die is used to cut ellipsoidal and hyperbolic-shaped from a single sheet of material and these shapes are overlaid to form an absorbent structure. The shapes are chosen such that there is no waste of the material and yet the resulting absorbent structure is of a useful shape. Methods are also disclosed whereby two sets of rotary dies are used to simultaneously cut two sheets of material into an arcuate segment and the arcuate segments are overlaid atop each other to form useful absorbent structures. In either embodiment, powders such as superabsorbents may be added to one or more of the surfaces of the components used to construct the absorbent structures.

10 Claims, 3 Drawing Sheets

5,562,793

METHODS AND APPARATUS FOR MAKING MULTI-LAYER ABSORBENT PRODUCTS

This is a division of application Ser. No. 08/204,127, filed Mar. 2, 1994.

The present invention relates to methods and apparatus for making absorbent products and to absorbent products themselves. More specifically, the present invention relates to absorbent products formed from two or more layers of material.

BACKGROUND OF THE INVENTION

The production of absorbent products such as sanitary napkins is a highly developed art that encompasses numerous techniques for cutting and assembling various layers of materials into absorbent product. As with any consumer product produced in high volumes, two considerations are of paramount importance, speed and efficiency. Speed is enhanced by making the production process as continuous as possible. Ideally rolls of material are fed into one end of a production system and finished product emerges. For example, U.S. Pat. No. 4,432,746 discloses a web segmenting apparatus that cuts a running web into discrete articles. Other systems for cutting webs either continuously or discontinuously are known.

One aspect of efficiency is the full utilization of raw materials, thus sheet material should be cut to minimize excess design scrap or trim waste. However, many types of absorbent products are cut to shapes specifically chosen to conform to the parts of the body to which they are applied. For example, U.S. Pat. No. 3,488,778 (Goujon et al.) discloses the pattern required to fabricate panties. As seen in FIGS. 2-3 of that patent, however, there is a great deal of material wasted when this pattern is cut.

There is therefore a continuing need to provide efficient processes for making absorbent articles. Moreover, it would be desirable to construct absorbent articles with as little waste material as possible. It is therefore an object of this invention to provide absorbent articles and apparatus and methods for making them that utilize materials efficiently and that lend themselves to being operated continuously.

SUMMARY OF THE INVENTION

Methods of forming absorbent structures are disclosed that include the steps of feeding a sheet of material into a die and cutting substantially ellipsoidal portions from the material at evenly spaced intervals, thereby leaving substantially hyperbolic portions between the ellipsoidal portions. At least one ellipsoidal portion is then placed atop at least one of the hyperbolic portions to create an absorbent structure. By using the methods of the present invention, an absorbent structure is formed with substantially no waste by using the entire sheet of material from which the absorbent structure is formed. In a preferred embodiment, the methods of the present invention include the step of feeding material of a predetermined width into a rotary die to provide a continuous process. In certain embodiments of the invention, the additional step of spraying a powder across the material is added. This permits an absorbent powder for the like to be added to the components of the absorbent structure. Most preferably, the faces of the ellipsoidal and hyperbolic portions that have been sprayed with a powder are placed face to face to form an absorbent structure.

An alternative embodiment of the method of the present invention includes the steps of feeding a first sheet of material into a first die and cutting an arcuate section from the material while simultaneously feeding a second sheet of material into a second die and cutting an arcuate section from this sheet of material. The two arcuate sections are placed atop one another to form a substantially ellipsoidally-shaped overlapping section within an absorbent structure. In this embodiment, rotary dies are again preferably used and in certain embodiments, a powder may be applied to the material.

The present invention also discloses products made using the above-described method and apparatus including sanitary napkins, panty shields and diapers. Thus, in a first embodiment, an improved product is disclosed that comprises a hyperbolic-shaped layer of material and an ellipsoidal-shaped layer of material that is disposed atop the hyperbolic-shaped layer wherein due to being cut from the same sheet of material the hyperbolic and ellipsoidal layers have a substantially identical curvature along at least part of their perimeter.

DETAILED DESCRIPTION OF THE PREFERRED EMBODIMENTS

The present invention most preferably takes advantage of the manufacturing efficiencies inherent in the use of a rotary die. As understood by those of ordinary skill, a rotary die permits a sheet of material to be continuously fed into the die and cut into desired shapes. A typical rotary die useful with the present invention is in the form of a steel rule die that is formed around a cylinder. The surface of the cylinder may carry one or more of the shapes that are being cut. It will be understood, however, that a rotary die is not the only apparatus capable of using the general methods disclosed herein to form products as disclosed. Although productivity will be sacrificed, other types of dies can be readily implemented to cut the shapes disclosed herein. Accordingly, it will be realized that the embodiments of the present invention depicted in the accompanying figures are meant to illustrate preferred embodiments of the present invention.

As used herein the term "absorbent product" is meant to apply to any product that is used to absorb and retain body fluids. Examples of such products are sanitary napkins and panty shields, infant diapers and adult incontinent diapers, and wound dressings.

Figure 1:
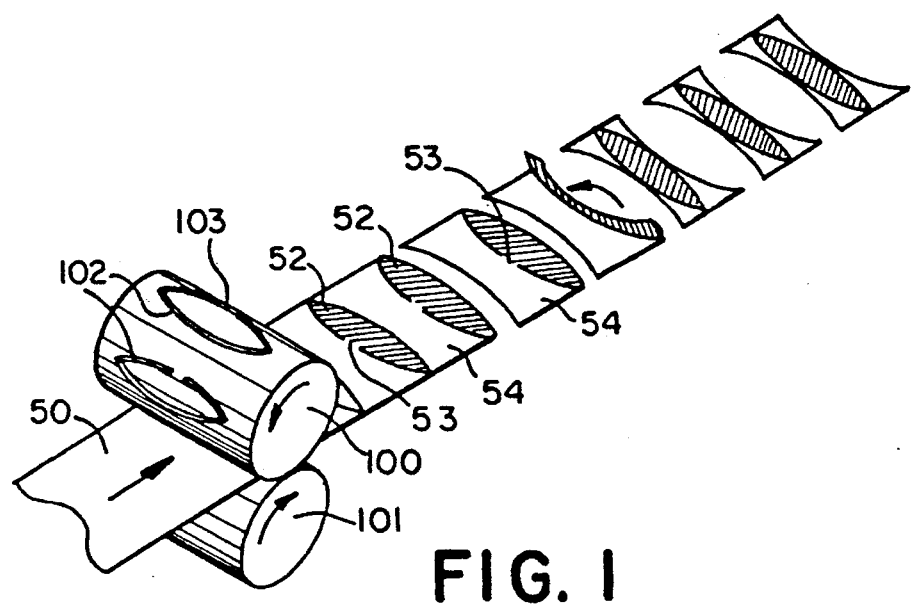
FIG. 1 is a partial perspective view of a portion 20 of a rotary die apparatus as used with the present invention and products made thereby.

Referring now to FIG. 1, there is shown a strip of material 50 from which an absorbent structure will be formed. The material 50 can be either hydrophilic or hydrophobic and may be chosen from any of the materials used to construct absorbent products. Thus, for example, if the resulting structure is itself used as an absorbent product, the material 50 could be an absorbent web of cellulosic fiber. If, however, the resultant product were to be integrated with other layers, the methods and apparatus disclosed herein would be useful to form a top sheet or other non-absorbent portion of the resulting absorbent product.

The sheet of material 50 is preferably fed in between a pair of counter-rotating rollers 100, 101. The top roller 100 is most preferably a rotary die and has one or more die segments 102 formed on its surface. The lower roller 101 typically acts as a platen and has a smooth surface, however, in certain embodiments cooperating die portions may also be formed on the lower roller 101. The rollers 100,101 are in close proximity and as the material 50 passes between them, it is cut in the shape of the die segments 102. For each cut, however, two portions of material are formed. As seen in FIG. 1, if the die segment 102 is substantially elliptical in shape, the material is cut into a series of elliptical portions 52 with a series of hyperbolic portions 54 between the elliptical portions 52. As used herein, geometric terms such as elliptical and hyperbolic are meant in the general sense and are not intended to be limited to the precise mathematical curves described by such terms. It should be noted that in the preferred embodiment illustrated in FIG. 1 a small gap 103 in the cutting edge of the die segment 102 results in a connecting portion 53 that connects one elliptical portion 52 to one hyperbolic portion 54. The two portions 52,54 may be joined by any conventional means, e.g., pressure, heat bonding, adhesives, hydrogen bonding, or may be loosely overlaid and retained together by another structure.

One aspect of the present invention illustrated in FIG. 1 is that as the material 50 is cut, there is essentially no waste material or selvage between the elliptical portions 52 and the hyperbolic portions 54. In other words, the area of the two portions 52,54 is approximately 100% of the area of the uncut material 50. The present invention takes advantage of this result by choosing the relative size and shape of each portion 52,54 such that they may be overlaid upon one another to produce a useful absorbent article. The specific example shown in FIG. 1 is an absorbent structure suitable for placement in the perineal area of a user when the material 50 from which it is formed is an absorbent material. The "hourglass" shape of the hyperbolic portion 54 permits comfortable placement over substantially the entire area, while the overlying ellipsoidal portion provides additional absorbency in the area where fluid discharge is typically the greatest.

Figure 2:
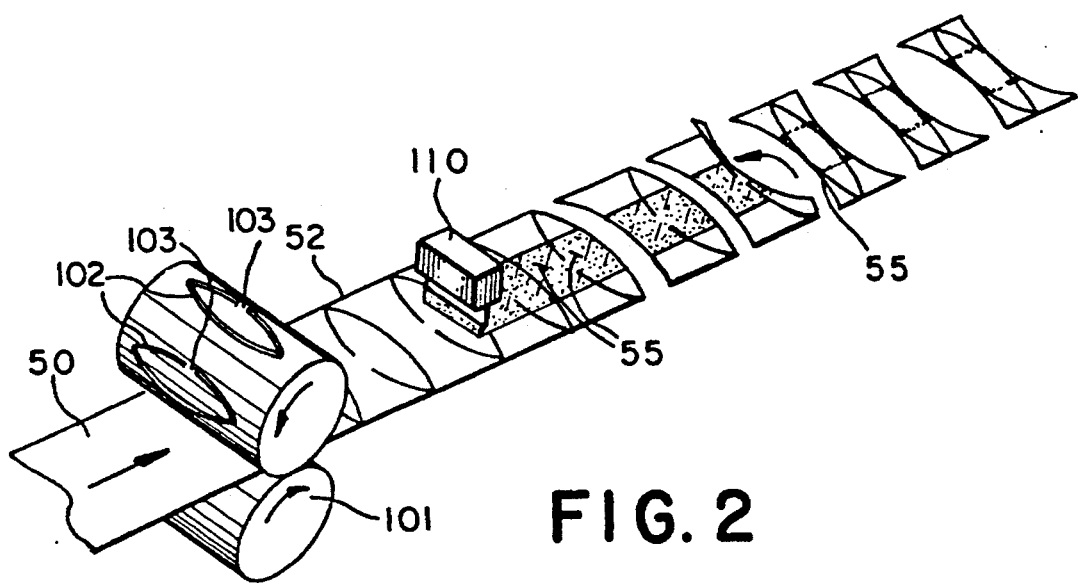
FIG. 2 is a partial perspective view of a portion of a rotary die apparatus, similar to that shown in FIG. 1, and also illustrating the application of a powder to cut sections of material.

Referring now to FIG. 2, an embodiment of the present invention similar to that shown in FIG. I is illustrated that includes the addition of a powder to the portions 52,54 of material 50 formed after cutting. In the preferred embodiment illustrated, a powder depositing device 110 such as a sprayer is positioned above the array of cut portions 52,54. A powdered material 55 is applied as shown to both the portions 52,54, preferably over an area of less than their full width. When the portions 52,54 are brought together, the powdered material 55 is substantially entrapped between the layers of the portions 52,54. This embodiment would therefore permit the addition of a superabsorbent powder to increase the absorbency and fluid retention characteristics of the resulting absorbent structure. Alternatively, other powdered materials such as antibiotics, disinfectants or deodorizers may be added. Additionally, although powdered materials represent a preferred embodiment, it will be understood that non-powdered sprayable materials including liquids, sols and gels may also be applied in the manner shown in FIG. 2. Finally, the spraying of the powdered material or other material may be undertaken in different patterns or performed intermittently. In the latter instance, it is possible to synchronize the intermittent spray with the movement of the portions 52,54 such that only selected ones of either the elliptical or the hyperbolic portions 52,54 are sprayed.

Figure 3:
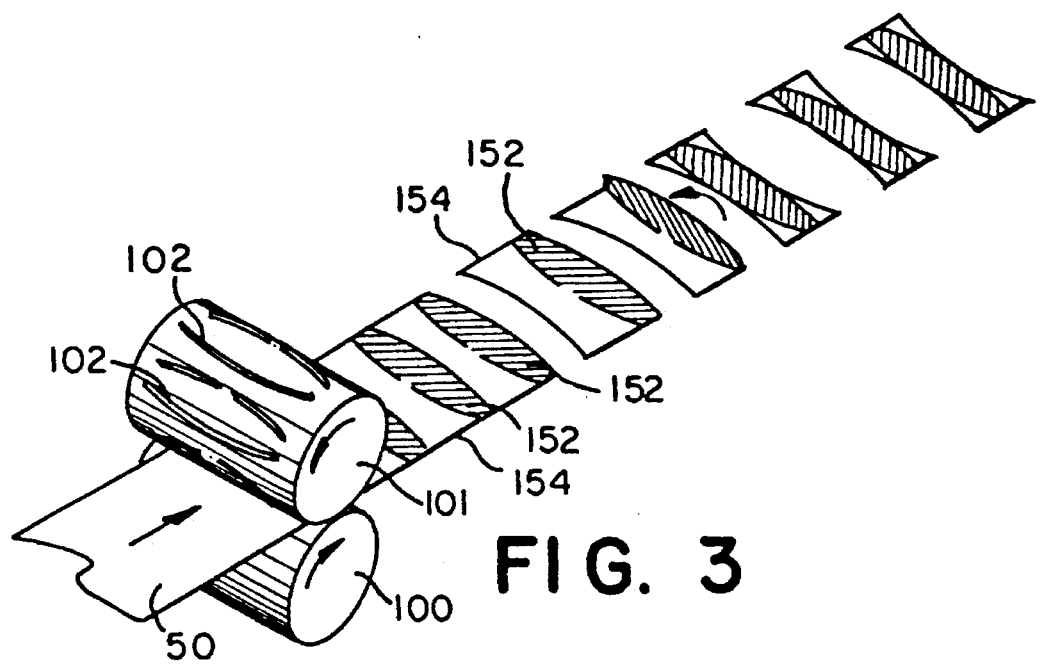
FIG. 3 is a partial perspective view of a portion of a rotary die apparatus as used with the present invention, similar to that shown in FIG. 1, and also illustrating an alternate embodiment of products made thereby.

FIGS. 1–2 illustrate embodiments of the present. invention wherein the elliptical portions 52 extend across the full width of the material such that their endpoints are located along the edges of the material 50. However, as shown in FIG. 3, embodiments of the present invention are also contemplated wherein the radius of curvature of the die segments 102 on the rotary die roller 101 is greater than that shown in FIGS. 1–2. As a result, the elliptical portions 152 cut in this embodiment do not come to a "point" but instead have square edges. As a result, the hyperbolic portions 154 of this embodiment also have a greater radius of curvature, i.e., they are less curved. However, as seen in FIG. 3, the portions 152,154 will again overlie each other without any waste and form a useful absorbent structure that is of double thickness in certain areas.

Figure 4:
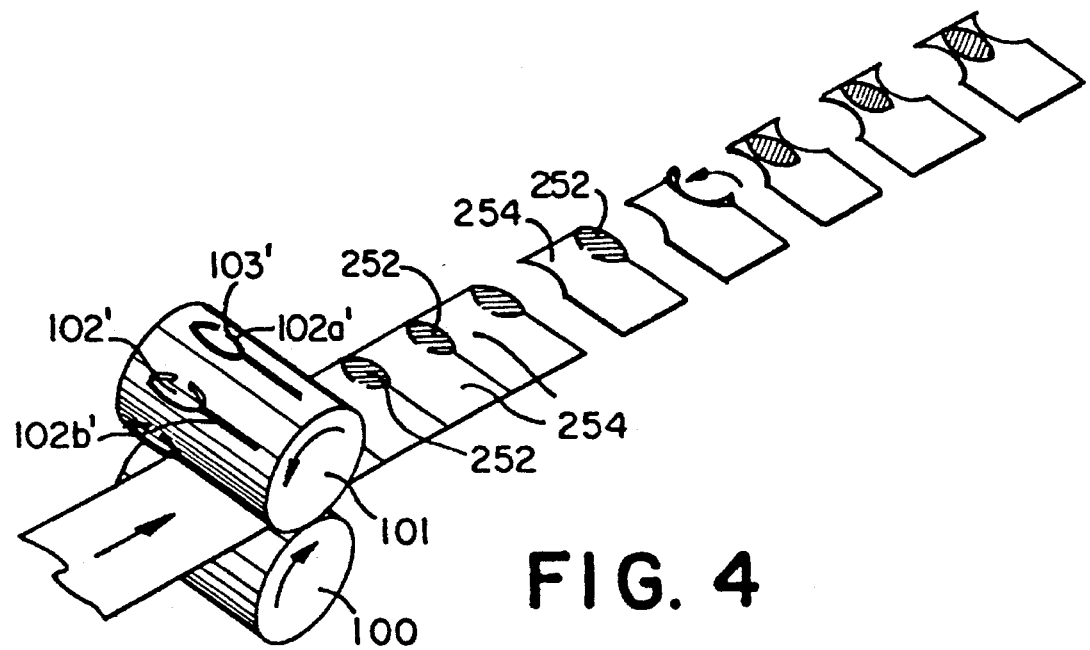
FIG. 4 is a partial perspective view of a portion of a rotary die apparatus as used with the present invention, similar to that shown in FIG. 1, and also illustrating an another alternate embodiment of products made thereby.

Another alternate embodiment of the present invention is illustrated in FIG. 4. In this embodiment, the design of the die segments 102' on the rotary die roller 101 are somewhat different from those shown in FIGS. 1–3 and described above. In this embodiment, a elliptical portion 102a' is provided at one end of a straight segment 102b'. As described above, a small gap 103' is left in the elliptical portion 102a'. Thus, as shown in FIG. 3, as the material 50 moves beneath the rotary die roller 101 elliptical portions 252 of a relatively small radius of curvature that do not extend across the entire width of the material 50 are formed. A hyperbolic (and partially rectangular) portion 254 remains between and preferably connected to the elliptical portions 252. By folding the elliptical portion 252 in the manner illustrated to overlie the hyperbolic portion 254, an absorbent structure results that has a double thickness over a relatively small area. It will be recognized that the products made using this embodiment of the invention are made with no waste and, depending on their size, would be particularly useful as either an infant diaper or an incontinent adult diaper. The double thickness portion of the structure is preferably positioned to lie near the area of waste discharge when worn. If desired the square portion may be adapted by folding or further cut to be secured to the rest of the structure and surround the hips of the wearer. Of course, sanitary napkins, panty shields and other absorbent products can be made in accordance with this embodiment of the invention.

Figure 5:
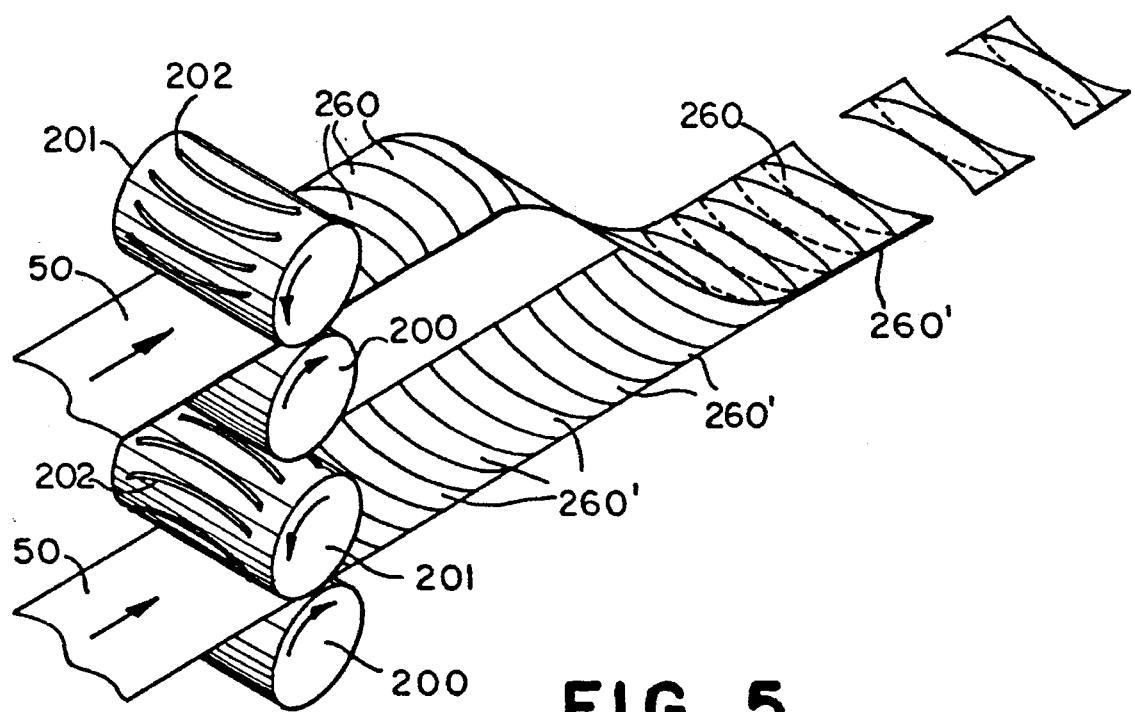
FIG. 5 is a partial perspective view of a portion of a pair of rotary die apparatus as used with certain embodiments of the present invention, and also illustrating products made thereby.

In addition to the hyperbolic/elliptic shapes described above, new and useful improvements can be made using the embodiment of the invention illustrated in FIG. 5. As illustrated, in a preferred version of this embodiment of the invention, two sets of identical rollers 200,201 are arranged as a pair of rotary dies that are each fed a length of material 50. The upper roller 201 of each pair has at least one arcuate die segment 202 formed on its surface. As a result, as each of the two lengths of material 50 passes between the sets of rollers 200,201, it is cut to form á plurality of arcuate portions 260,260' as shown. Most preferably, these arcuate portions 260,260' have parallel sides and extend across the full width of the material 50. By orienting the curvature of each of the arcuate portions 260,260' in opposite directions, i.e., turned 180°, when they are laid upon one another a substantially hyperbolic absorbent structure results that is similar to that formed using the embodiment illustrated in FIG. 1 in that an elliptic section of double thickness is centrally located.

The embodiment of the invention shown in FIG. 5 admits to many variations. For example, the two lengths of material 50 may be different types of material, or a powder or other form of another material may be sprayed on any part of the structure, as illustrated, for example, in FIG. 2. it will be realized that it is also possible to create the structure shown in FIG. 5 using a substantially similar technique that includes only one rotary die 200,201. In such an embodiment, the alternate ones of the arcuate shapes 260 cut from a single length of material 50 would be reversed relative to one another in a separate step to result in the ultimate orientation shown in FIG. 5.

Although certain embodiments of the present invention have been set forth herein with particularity, it will be realized by those of ordinary skill that numerous adaptations and modifications to the methods, apparatus and products disclosed herein are readily made. For example, dies other than the rotary dies may be used to cut substantially similar shapes to result in products substantially similar to those illustrated. These embodiments, however, will not depart from the spirit of the inventive concepts disclosed herein. Accordingly, reference should be made to the appended claims in order to ascertain the full scope of the present invention.

What is claimed is:

1. A method of forming absorbent structures comprising the steps of:

feeding a sheet of a material into a die;

cutting substantially ellipsoidal portions from the material at evenly spaced intervals, leaving substantially hyperbolic portions therebetween; and, placing at least one ellipsoidal portion atop at least one hyperbolic portion to form the absorbent structure, and wherein the material has a width and the step of cutting the substantially ellipsoidal portions comprises cutting across the full width of the material.

2. The method of claim 1, wherein the step of feeding comprises feeding the material into a rotary die to continuously cut the material.

3. The method of claim 1 further comprising the step of applying powder to the material.

4. The method of claim 3, wherein the step of applying powder to the material comprises applying powder to a surface of the ellipsoidal portions and a surface of the hyperbolic portions, and further comprises the step of placing the surface of at least one ellipsoidal portion onto the surface of at least one hyperbolic portion such that the powder is between the at least one ellipsoidal portion and the at least one hyperbolic portion to form an absorbent structure comprising a central layer of powder.

5. The method of claim 4, wherein the step of applying powder is carried out intermittently.

6. The method of claim 1 wherein the die has an elliptical portion and a straight segment and wherein the step of cutting the substantially ellipsoidal portions comprises cutting across less than the full width of the material and the straight segment cuts across a remainder of the width of the material such that the full width of the material is cut.

7. A method of forming an absorbent structure comprising the steps of:

feeding a first sheet of material into a first die;

cutting an arcuate section from the first sheet of material;

feeding a second sheet of material into a second die;

cutting at least one arcuate section from the second sheet of material;

placing at least one arcuate section from the first sheet of material atop at least one arcuate section from the second sheet of material;

wherein the first and second sheets of material each have respective widths and the steps of cutting arcuate sections comprises cutting across the full width of the first and second sheets of materials; and wherein a substantially ellipsoidally shaped absorbent structure is formed.

8. The method of claim 7, wherein the steps of feeding the first and second sheets of materials comprises the step of feeding the first sheet of material into a first rotary die and feeding the second sheet of material into a second rotary die.

9. The method of claim 7 further comprising the step of applying powder to at least one of the first or second sheets of material.

10. A method of forming an absorbent structure comprising the steps of:

feeding a sheet of material into a die;

cutting at least two curved portions from the sheet of material;

placing one of the curved portions atop a second curved portion to form the absorbent structure, wherein the material has a width and wherein the step of cutting the at least two curved portions comprises cutting the material across its entire width.

* * * * *